United States Patent
Cuffaro et al.

(10) Patent No.: US 7,434,286 B2
(45) Date of Patent: Oct. 14, 2008

(54) POWERED TOOTHBRUSH WITH IMPROVED ERGONOMICS

(75) Inventors: Dan Cuffaro, Melrose, MA (US); Christine Enderby, Chelsea, MA (US)

(73) Assignee: Colgate-Palmolive Company, New York, NY (US)

( * ) Notice: Subject to any disclaimer, the term of this patent is extended or adjusted under 35 U.S.C. 154(b) by 517 days.

(21) Appl. No.: 10/374,325

(22) Filed: Feb. 26, 2003

(65) Prior Publication Data

US 2004/0163191 A1 Aug. 26, 2004

(51) Int. Cl.
*A46B 5/02* (2006.01)
*A61C 17/22* (2006.01)

(52) U.S. Cl. ................... 15/22.1; 15/28; D4/101
(58) Field of Classification Search ............ 15/22.1, 15/23, 28; D4/100–102, 104, 109, 138
See application file for complete search history.

(56) References Cited

U.S. PATENT DOCUMENTS

| | | | |
|---|---|---|---|
| 1,997,362 A | 4/1935 | Van Fleet | |
| 2,278,365 A | 3/1942 | Daniels | |
| D204,127 S | 3/1966 | Syvertson | |
| 3,241,168 A * | 3/1966 | McMaster et al. ......... | 15/22.1 |
| 3,242,516 A * | 3/1966 | Cantor ..................... | 15/28 |
| 3,699,952 A | 10/1972 | Waters et al. | |
| 3,757,419 A | 9/1973 | Hopkins | |
| 3,822,432 A | 7/1974 | Skinner | |
| D237,187 S | 10/1975 | Fattaleh | |
| 4,060,870 A | 12/1977 | Cannarella | |
| 4,179,814 A | 12/1979 | Montanio | |
| 4,420,851 A | 12/1983 | Wiener | |
| D278,764 S | 5/1985 | Olsen | |
| 4,603,448 A | 8/1986 | Middleton et al. | |
| D294,885 S | 3/1988 | Mollenhoff | |
| 4,845,796 A | 7/1989 | Mosley | |
| 4,974,278 A | 12/1990 | Hommann | |
| 5,054,149 A * | 10/1991 | Si-Hoe et al. ......... | 15/28 |
| D321,285 S | 11/1991 | Hirabayashi | |
| 5,173,983 A | 12/1992 | Le | |

(Continued)

FOREIGN PATENT DOCUMENTS

FR  2 182 535  12/1973

(Continued)

Primary Examiner—Mark Spisich
(74) Attorney, Agent, or Firm—Michael J. Wallace, Jr.

(57) ABSTRACT

A powered toothbrush which has been designed for improved ergonomics and for assisting the user in using a powered brush in an improved and gentler manner. The powered toothbrush includes a handle portion having a base member at one end thereof. A neck portion extends from the other end of the handle portion with the head coupled to the neck portion. The head includes at least one bristle carrier connected to a drive shaft rotating the at least one bristle carrier in a first rotatable direction. In order to improve the ergonomics and stability of the powered toothbrush, the handle portion is formed asymmetrical about the longitudinal axis of the powered toothbrush and the base member of the handle portion is substantially flat. In this ergonomically-designed powered toothbrush, the width of the base member is less than the greatest width of the handle portion, the depth of the base member is less than the greatest depth of the handle portion, and the height dimension of the neck portion is greater than the height dimension of the handle portion.

3 Claims, 7 Drawing Sheets

U.S. PATENT DOCUMENTS

| | | |
|---|---|---|
| D334,842 S | 4/1993 | Lemon et al. |
| 5,259,086 A * | 11/1993 | Fong ........................... 15/105 |
| 5,311,633 A | 5/1994 | Herzog et al. |
| 5,341,534 A | 8/1994 | Serbinski et al. |
| 5,406,664 A | 4/1995 | Hukuba |
| D361,433 S | 8/1995 | Yang |
| 5,467,494 A | 11/1995 | Müller et al. |
| 5,504,961 A | 4/1996 | Yang |
| 5,625,916 A | 5/1997 | McDougall |
| 5,689,850 A | 11/1997 | Shekalim |
| 5,836,030 A | 11/1998 | Hazeu et al. |
| 5,901,397 A | 5/1999 | Häfele et al. |
| 6,138,310 A | 10/2000 | Porper et al. |
| 6,202,242 B1 | 3/2001 | Salmon et al. |
| D440,766 S | 4/2001 | Hartwein et al. |
| 6,230,717 B1 | 5/2001 | Marx et al. |
| D444,303 S | 7/2001 | Reille |
| 6,360,395 B2 | 3/2002 | Blaustein et al. |
| D455,010 S | 4/2002 | Kling |
| 6,363,565 B1 * | 4/2002 | Paffrath ........................ 15/28 |
| D458,027 S | 6/2002 | Ferber et al. |
| D462,174 S | 9/2002 | Schaber |
| 6,446,294 B1 | 9/2002 | Specht |
| 6,453,497 B1 | 9/2002 | Chiang et al. |
| 2002/0039720 A1 | 4/2002 | Marx et al. |
| 2002/0092104 A1 | 7/2002 | Ferber et al. |
| 2002/0124333 A1 | 9/2002 | Halfiger et al. |
| 2003/0000031 A1 | 1/2003 | Zhuan |
| 2004/0007244 A1 | 1/2004 | Harms |

FOREIGN PATENT DOCUMENTS

| | | |
|---|---|---|
| WO | 97/04719 * | 2/1997 |
| WO | WO 02/45919 A | 6/2002 |

* cited by examiner

POWERED TOOTHBRUSH WITH IMPROVED ERGONOMICS

BACKGROUND OF THE INVENTION

1. Field of the Invention

The present invention relates to powered toothbrushes, and more particularly, to a powered toothbrush having improved ergonomics.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of the toothbrush by a user, provide superior cleaning than manual toothbrushes. Typically, powered toothbrushes are powered by disposable or rechargeable batteries that power an electric motor that in turn drives a toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw bones, and each row of teeth consequently has a convex outer curve and a concave inner curve. Individual teeth often have extremely complex surfaces, with areas that may be flat, concave or convex. The more precise conformation between the bristles and the tooth surface, the more effective the toothbrush may be in cleaning, whitening and/or stimulating.

Although powered toothbrushes such as those described immediately above provide advantages over manual toothbrushes, they are not designed for ergonomic comfort and ease of use and are not typically designed to assist the user in using a powered brush in an improved and gentler manner as they should. In this regard, the recommended method of utilizing a powered toothbrush can be described as (1) moving the bush head slowly from tooth surface to tooth surface; and/or (2) concentrating the cleaning to one tooth at a time. In contrast, a manual toothbrush is used as a scrubbing tool where the motion is powered by the user resulting in a less gentler use.

Moreover, the configuration of the base of the existing powered toothbrushes does not typically provide for stability of the toothbrush when supported in an upright condition and provides a higher center of gravity which hinders ergonomic considerations. Currently, the width of a typical powered toothbrush is between 20 to 30 mm and the depth of a typical powered toothbrush is between 30 to 35 mm.

OBJECTS OF THE INVENTION

Therefore, it is an object of the invention to provide a powered toothbrush which avoids the aforementioned deficiencies of the prior art.

It is also an object of this invention to provide a powered toothbrush with improved ergonomic design.

It is another object of this invention to provide a powered toothbrush which has a shorter and stubbier handle which will assist the user in using a powered brush in an improved and gentler manner.

It is still another object of this invention to provide a powered toothbrush with a stable base.

It is yet another object of this invention to provide a powered toothbrush which is reduced in size.

It is still a further object of the present invention to provide a powered toothbrush which has a lower center of gravity.

It is still another object of this invention to provide a powered toothbrush which uses a conventional motor and batteries.

It is yet another object of this invention to provide a powered toothbrush which reduces noise and vibration.

It is yet still a further object of this invention to provide a powered toothbrush which simplifies user interface.

Various other objects, advantages and features of the present invention will become readily apparent from the ensuing detailed description and the novel features will be particularly pointed out in the appended claims.

SUMMARY OF THE INVENTION

This invention relates to a powered toothbrush which has been designed for improved ergonomics and for assisting the user in using a powered brush in an improved and gentler manner. The powered toothbrush of this invention includes a handle portion having a base member at one end thereof. A neck portion extends from the other end of the handle portion with a head coupled to the neck. The head includes at least one bristle carrier connected to a drive shaft for moving the at least one bristle carrier in a first rotatable direction.

This powered toothbrush has a longitudinal axis which is coaxial with the handle and neck portions. In order to improve the ergonomics of the powered toothbrush, the handle portion is formed asymmetrically about the longitudinal axis and the base member of the handle portion is substantially flat to provide a stable base for support when the powered toothbrush is not in use and stored on a horizontal surface.

In addition, each of the base member and the handle portion have a width which intersects the longitudinal axis and is parallel to the bristle carrier. In this ergonomically-designed powered toothbrush, the width of the base member is less than the greatest width of the handle portion Moreover, each of the base member and the handle portion have a depth which intersects the longitudinal axis and is perpendicular to the bristle carrier. In this powered toothbrush, the depth of the base member is less than the greatest depth of the handle portion. Further, the handle and the neck portions have a height dimension which is parallel to the longitudinal axis. In this powered toothbrush, the height dimension of the neck portion is greater than the height dimension of the handle portion. This configuration provides a short and stubbier design which has a lower center of gravity compared to existing elongated powered toothbrushes so as to provide improved gripping/ergonomics during use.

In accordance with one of the objects of the present invention, the powered toothbrush of this invention uses a conventional motor and at least one battery to power the motor which drives the drive shaft which moves the bristle carrier in the first rotational direction. In one embodiment of this ergonomic design, two AAA batteries are accommodated within the handle portion in an upright side-by-side relationship. In another embodiment, two AAA batteries for powering the motor for driving the drive shaft can be accommodated upright and have an end thereof supported adjacent to the base member. In this embodiment, the motor is provided between the two AAA batteries. However, the designs can be adapted to use batteries of various sizes and combinations, such as one AA battery, two AA batteries, one 9V battery, and one C battery.

In order to simplify user interface, the powered toothbrush of this invention includes a single on/off switch for activating/deactivating the motor which is provided along a face of the handle portion in a thumb depression.

BRIEF DESCRIPTION OF THE DRAWINGS

The following detailed description given by way of example, but not intended to limit the invention solely to the specific embodiments described, may best be understood in connection with the accompanying drawings in which.

DETAILED DESCRIPTION OF CERTAIN PREFERRED EMBODIMENTS OF THE PRESENT INVENTION

Referring now to the drawings, wherein like reference numerals represent like features in the several views, two preferred embodiments of a powered toothbrush in accordance with the teachings of the present invention are shown in FIGS. 1-12. In particular, FIGS. 1-6 relate to a "pod-like" design for a powered toothbrush. FIGS. 7-12 refer to a "slim" design for a powered toothbrush. These designs will be hereinafter referred to respectively as the "pod" and "slim" designs. Both of the "pod" and "slim" designs provide for a powered toothbrush with improved ergonomics as well as a powered toothbrush which has a shorter and stubbier handle which assists the user in using a powered brush in an improved and gentler manner. However, designs other than the specific "pod" and "slim" designs set forth herein are also contemplated which would similarly improve the ergonomics for a powered toothbrush and be in accordance with the teachings of the present invention.

Figure 1:
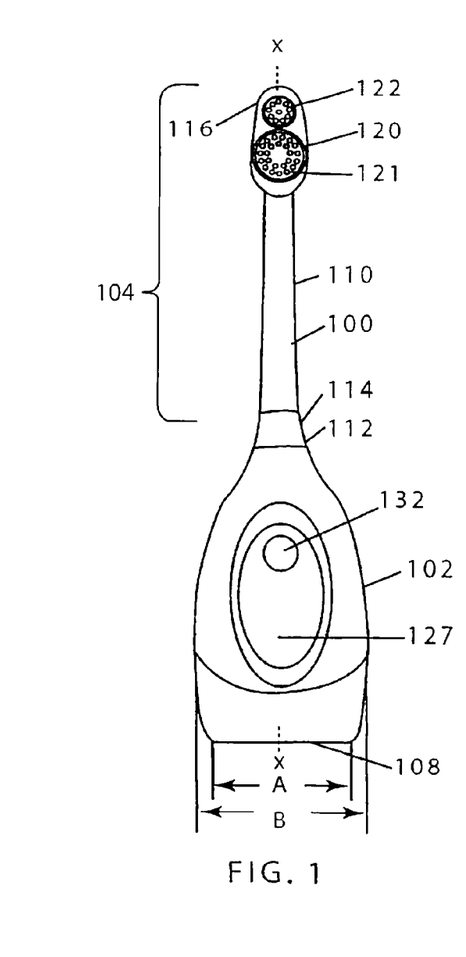
FIG. 1 is a front elevational view of a preferred embodiment of a powered toothbrush in accordance with the teachings of the present invention.

As is shown in FIG. 1, the "pod" powered toothbrush 100 includes a handle portion 102 at a proximal end thereof that defines an interior compartment for housing various toothbrush components, and a brush section 104 that is defined by a neck portion 110 that terminates in a head 120 at a distal end of toothbrush 100. The handle portion 102 has a free proximal base support end member 108 and an opposite neck end 112. The neck portion 110 generally includes a first end 114 and a second end 116 with the first end 114 being located at the neck end 112 of the handle portion 102 and second end 116 being located at the head 120. In other words, the neck portion 110 is the portion of the powered toothbrush 100 that extends between handle 102 and head 120. The neck portion 110 also defines an interior compartment 111 (see FIGS. 4 and 5) for housing various components of the toothbrush, such as an impeller fixed to a driveshaft. As is shown in FIG. 1, the handle portion 102 and neck portion 104 are generally aligned along the longitudinal axis x-x of the powered toothbrush 100.

Figure 2:
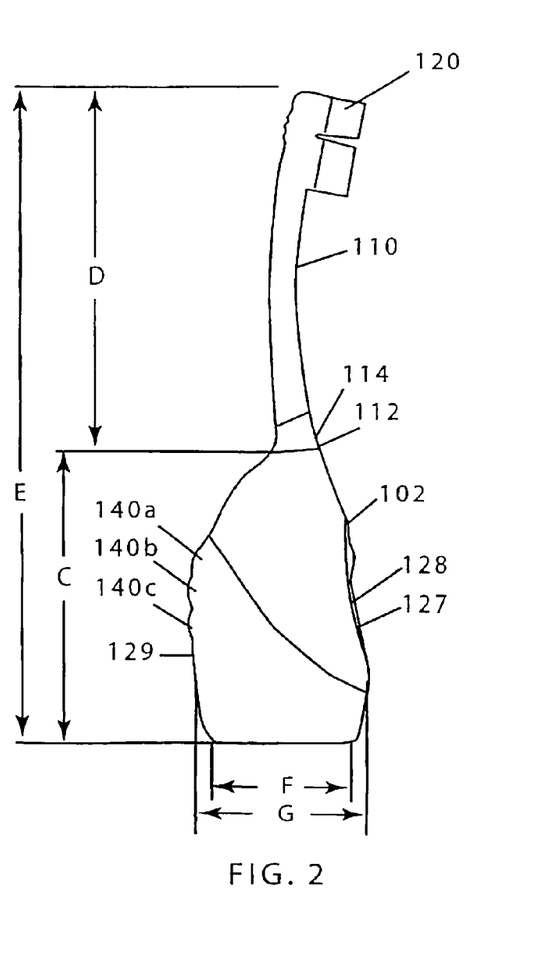
FIG. 2 is a side elevational view of the powered toothbrush of FIG. 1.
Figure 3:
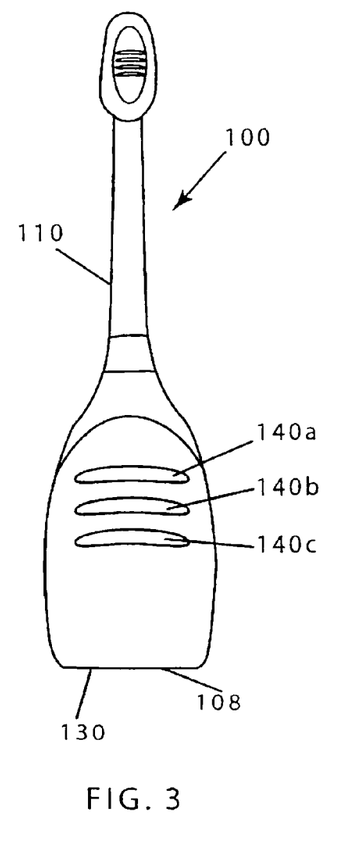
FIG. 3 is a rear elevational view of the powered toothbrush of FIG. 1.
Figure 4:
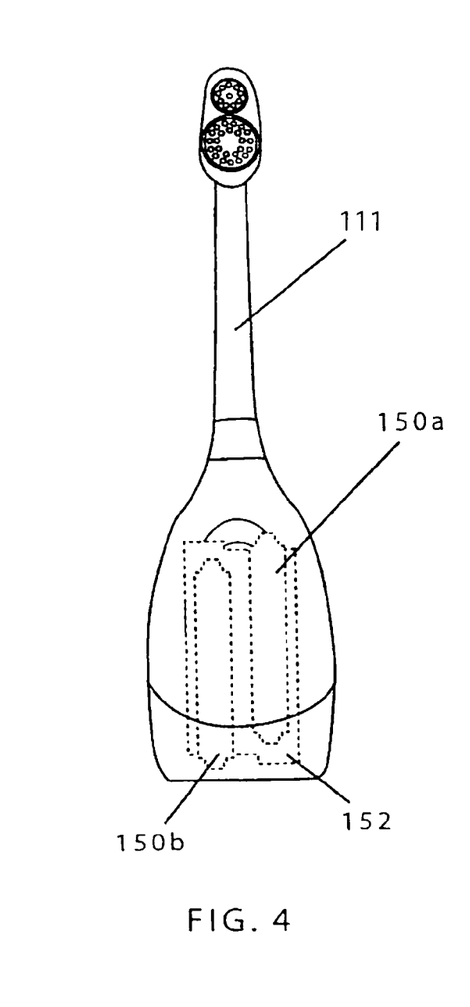
FIG. 4 is a front elevational view of the powered toothbrush of FIG. 1 exposing the position of the motor and batteries.
Figure 5:
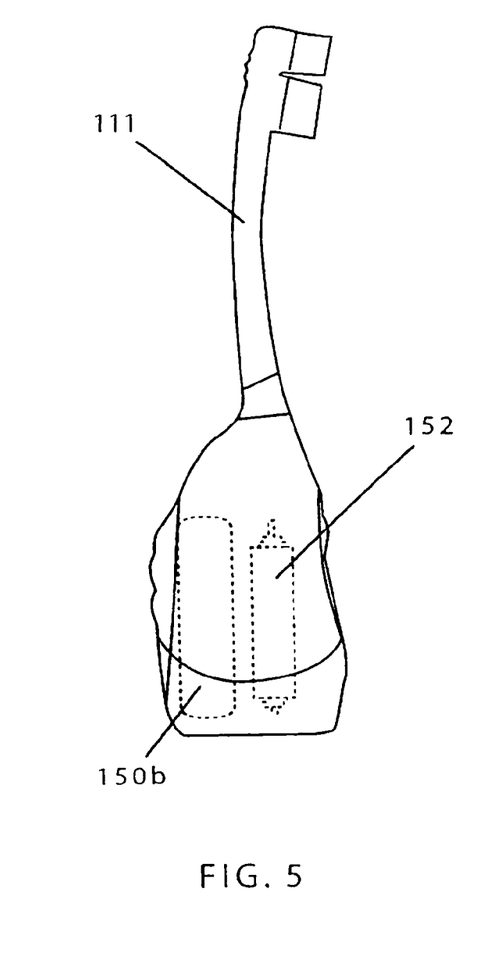
FIG. 5 is a side elevational view of the powered toothbrush of FIG. 1 exposing the position of the motor and batteries.
Figure 6:
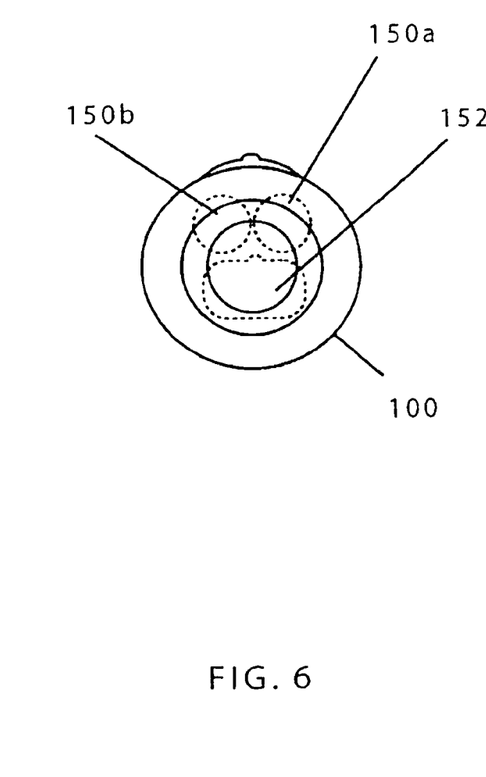
FIG. 6 is a bottom view of the powered toothbrush of FIG. 1 exposing the position of the motor and batteries.

The neck portion 110 and the handle portion 102 can be constructed as a unitary member by forming neck portion 110 integral to handle portion 102 at neck end 112 of the handle portion 102, or can be formed detachable from handle portion 102 at neck end 114 of neck portion 110. In accordance with this detachable embodiment, combined neck portion 110 and head 120 can be removed from the handle portion 102 to permit cleaning, servicing and/or interchanging of either handle 102 or the combined neck 110 and head 120 (brush section 104). When the neck portion 110 is formed to be detachable from handle 102, the first neck end 114 preferably includes a connector linkage (not shown) that is adapted to be detachably joined to handle portion 102 using traditional techniques. It will be appreciate that the point of attachment may be between the head portion 120 and the neck portion 110 such that the head 120 is of a refill type head. Furthermore, the head 120 is formed of at least a first bristle carrier 121 which rotates in first rotational direction. The head 120 may also include a second bristle carrier 122, as shown in FIGS. 1 and 2, which can either include stationary bristles, or rotate in the same direction as first bristle carrier 121, or in an opposite direction therefrom.

The powered toothbrush 100 includes a drive mechanism to effectuate certain movement of certain parts of the toothbrush, and more specifically for causing movement of the movable bristle carrier 121, and bristle carrier 122, if movable. One exemplary drive mechanism is disclosed in U.S. Pat. No. 5,625,916 to McDougall, which is incorporated herein by reference and includes a rotating drive shaft that extends at least through the neck portion 110 (i.e., through the inner compartment thereof). The drive shaft has one end that is operatively connected to a drive member, such as motor 152 (FIGS. 4-6), for imparting movement to the bristle carrier 121. Drive shaft can be formed with an opposing distal end that is bent such that the end is not axially aligned with the longitudinal axis of the drive shaft. In other words, the end is an offset crank end of the drive shaft and is configured to be received in a slot of head so that a 360° rotational movement of the shaft is transmitted into an oscillating back and forth rotational movement of the bristle carrier 121.

The drive mechanism for powered toothbrush 100 can be any type of drive, e.g., a rotating drive, an oscillating drive, an eccentric drive, an unbalanced-generated drive, a drive having one or more gearing mechanisms, and/or the like, that is capable of performing the intended function. The drive mechanism can be realized in the form of an electric motor or other type of motor and the movement generated by the drive can be imparted to one or more sections of the head or to other elements which can be present at the brush section, such as bristle tufts, elastomeric members. The movement can be imparted directly through a driving axle, such as a drive shaft or it can be imparted through a driving post attached to the driving axle. As will be explained in more detail below, when the toothbrush 100 includes an oscillating drive mechanism, the interior compartment of a handle 102 houses the motor 152 operatively connected to the drive shaft and a source to power the motor, such as the two AAA batteries 150a and 150b shown in FIGS. 4-6.

When the drive mechanism is actuated and the drive shaft is rotated, the movement of the crank end thereof imparts an oscillating back and forth movement of the bristle carrier 121 through an angle between about 10° to about 120° and in a preferred exemplary embodiment, the movement is through an angle of between 10° to about 30°, and in a most preferred embodiment is through an angle between about 10° to about 15°.

The dimensions of the "pod" design provide a powered toothbrush which is reduced in size. In addition, this toothbrush, based upon the dimensions to be given in more detail below, has a shorter and stubbier handle that existing powered toothbrushes which assists the user in using the powered brush in an improved and gentler manner. In addition, this "pod" design is improved ergonomically over existing powered toothbrushes.

As aforementioned, the longitudinal axis x-x of the "pod" design is coaxial with the handle and neck portions 102 and 110. The base member 108 has a width A (see FIG. 1) which intersects the longitudinal axis x-x and is parallel to the bristle carrier 121. In addition, the handle portion has a greatest width B (see FIG. 1) which intersects the longitudinal axis x-x and is parallel to the bristle carrier 121. As is shown in FIG. 1, the width A of the base member 108 is less than the greatest width B of the handle portion 102. In the "pod" design, the width of the base member is within the range of between approximately 20 to 50 mm, and most preferably 37 mm. The greatest width B of the handle portion 102 in the "pod" design is within the range of approximately 25 to 60 mm, and most preferably 43 mm.

In addition, each of the handle and neck portions 102 and 110 has a height dimension, respectively C and D in FIG. 2, which is parallel to the longitudinal axis x-x. In order to improve the ergonomics, and provide for a shortened design, the height dimension D of the neck portion 110 is greater than the height dimension C of the handle portion 102. In this "pod" design, the overall height E of the powered toothbrush is within the range of between approximately 140 to 180 mm, and most preferably 160 mm. The height dimension C of the handle portion 102 is within the range of between approximately 30 to 100 mm, and most preferably 70 mm. The height dimension of the neck portion 110 is within the range of between approximately 50 to 110 mm, and most preferably 90 mm.

Further, each of the base member 108 and the handle portion 102 have a depth which intersects the longitudinal axis x-x and is perpendicular to the bristle carrier 121. The depth of the base member 108 is designated by reference F in FIG. 2, and can be in the range of between approximately 20 to 50 mm, and most preferably 37 mm. The greatest depth of the handle portion 102 is represented by dimension G in FIG. 2, and can be in the range of between approximately 25 to 60 mm, and most preferably 43 mm.

Therefore, as discussed above, in this "pod" design, the width A of the base member 108 is less than the greatest width B of the handle portion 102. In addition, the depth F of the base member 108 is less than the greatest width G of the handle portion 102. Moreover, the height dimension D of the neck portion 110 is greater than the height dimension C of the handle portion 102. This combination of features provides for a powered toothbrush with a short and stubbier design than existing powered toothbrushes which thereby achieves a lower center of gravity compared to existing elongated powered toothbrushes such that the "pod" design herein more closely conforms to an overall hand grip and palm configuration of the user so as to provide a more accurate placement of the brush on the brushing surface, a more direct application of pressure to the brushing surface, and less stress on the user's wrist. The ergonomic design of the pod brush is also enhanced due to the handle portion 102 being formed asymmetrically about the longitudinal axis x-x of the powered toothbrush 100 and base member 108 being substantially flat which provides a stable base support, and thus, an improved stand-up feature when the powered toothbrush is not in use and stored on a horizontal surface.

As a result of this short and stubbier design, the two AAA batteries 150a and 150b for powering the motor 152 can be accommodated upright and each have a respective end supported adjacent to the base member 108. In addition, the motor 152 is provided between the two AAA batteries 150a and 150b. As a result of this design, less noise and vibration are generated in the "pod" designed toothbrush in comparison to existing powered toothbrushes having two coaxially aligned batteries placed in a narrow and elongated handle portion.

As is best shown in FIG. 2, in order to provide comfortable handling of the powered toothbrush 100 of the "pod" design, the front face 127 includes a concave depression 128. The concave depression 128 on the front face 127 of the handle portion 102 also includes a single on/off switch 132 extending therefrom. Since the user's thumb easily rests upon the concave depression 128, this "pod" design simplifies user interface. Moreover, the user's finger rest comfortably along undulations 140a, 140b, and 140c provided on the rear surface 129 of the "pod" design (see FIGS. 2 and 3). Although the on/off switch 132 is shown extending from a depression 128 on the front face 127 of the handle portion 102, the on/off switch 132 can also be provided on the side faces, bottom face, or rear face of the handle portion 102 and still be within the teachings of the present invention.

As aforementioned, the "slim" design for a powered toothbrush 100' is shown in FIGS. 7-12 of this application. The "slim" design of FIGS. 7-12 incorporates many of the same features as that of the "pod" design of FIGS. 1-6. For those features which are the same, or substantially the same in the "slim" design as in the "pod" design, that feature has been designated with a "'". For instance, the handle portion in the "slim" design has been designated by the reference numeral 102'. The above discussion of those related features from the "pod" design is incorporated herein for the "slim" design except as is specifically set forth below. As is set forth below, the "slim" design attains the same objects in terms of improved ergonomics and ease of use as the "pod" design.

Figure 7:
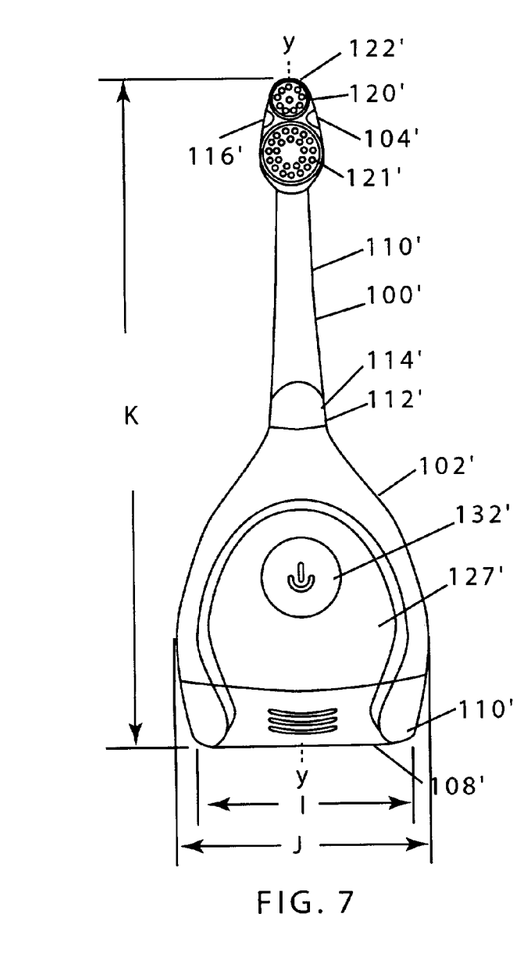
FIG. 7 is a front elevational view of another preferred embodiment of a powered toothbrush in accordance with the teachings of the present invention.

As shown in FIG. 7, the "slim" design has a longitudinal axis y-y which is coaxial with respect to the handle and neck portions 102' and 110'. The base member 108' and handle portion 102' have a width which intersects the longitudinal axis y-y and is parallel to the bristle carrier 121'. In the "slim" design, the width I of the base member 108' is less than the greatest width J of the handle portion 102'. The width I of the base member 108' in the "slim" design is within the range of between approximately 30 to 60 mm, and most preferably 50 mm. The greatest width J of the handle portion 102' is within the range of between approximately 40 to 70 mm, and most preferably 60 mm.

Figures 8, 9:
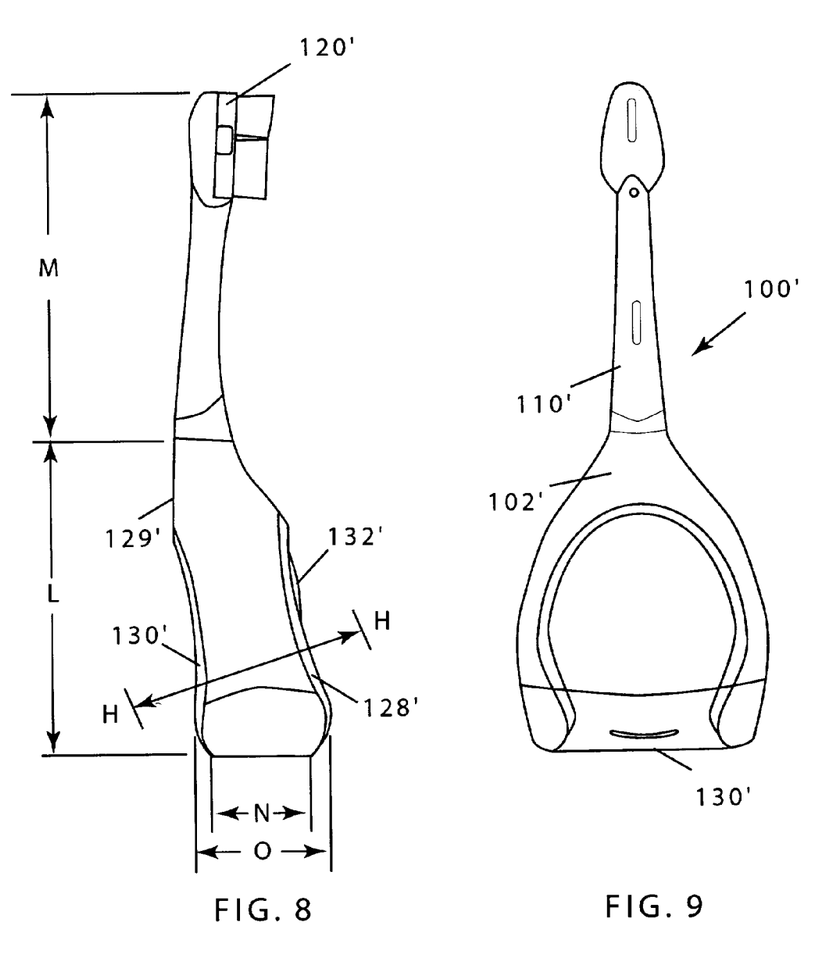
FIG. 8 is a side elevational view of the powered toothbrush of FIG. 7.
FIG. 9 is a rear elevational view of the powered toothbrush of FIG. 7.

In addition, each of the handle and neck portions 102' and 110' have a height dimension which is parallel to the longitudinal axis y-y of the "slim" design toothbrush 100'. As is shown in FIG. 8, the total height dimension of the "slim" design powered toothbrush 100' is designated by reference K. The height dimension of the handle portion 102' is designated by reference L whereas the height dimension of the neck portion 110' is designated by reference M. As is best shown in FIG. 8, the height dimension M of the neck portion 110' is greater than the height dimension L of the handle portion 102'. In the "slim" design, the overall height dimension K is within the range of between approximately 140 to 180 mm, and most preferably 160 mm. The height dimension M of the neck portion 110' is within the range of between approximately 50 to 110 mm, and most preferably 85 mm. The height dimension L of the handle portion 102' in the "slim" design is within the range of between approximately 30 to 100 mm, and most preferably 75 mm.

Moreover, each of the base member 108' and the handle portion 102' of this "slim" design have a depth (see N and O dimensions in FIG. 8) which intersects the longitudinal axis y-y and is perpendicular to the bristle carrier 121'. In the "slim" design, the depth of the base member 108' is less than the greatest depth O of the handle portion 102'. The depth of the base member 110' in the "slim" design is within the range of between approximately 15 to 40 mm, and most preferably 25 mm. The greatest depth O of the handle portion 102' in the "slim" design is within the range of between approximately 20 to 50 mm and most preferably 30 mm.

Therefore, as in the "pod" design, the "slim" design is configured such that the width I of the base member 108' is less than the greatest width J of the handle portion 102', the depth N of the base member 108' is less than the greatest width O of the handle portion 102', and the height dimension M of the neck portion 110' is greater than the height dimension L of the handle portion 102'. This combination of the dimensions provides a powered toothbrush with improved ergonomics and a powered toothbrush which has a shorter and stubbier handle to provide a lower center of gravity than existing elongated powered toothbrushes which assists the user in using a powered brush in an improved and gentler manner.

Moreover, the handle portion 102' of the "slim" design is asymmetrical about the longitudinal axis y-y and the base member 110' of the handle portion 102' is substantially flat which provides a stable base support and thus an improved stand up feature when the powered toothbrush is not in use and stored on a horizontal surface. This, in combination with the dimensions as set forth above, provides for a powered toothbrush which more closely conforms to an overall hand grip and the palm configuration of the user than existing powered toothbrushes for an accurate placement of the brush on the brushing surface, a more direct application of pressure to the brushing surface, and less stress on the user's wrist.

Figure 10:
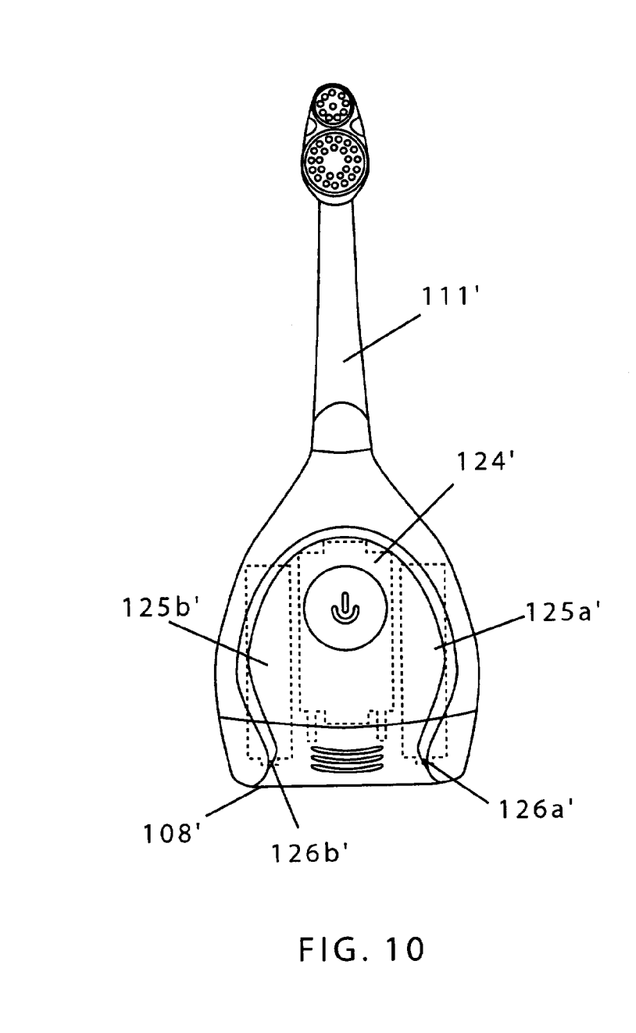
FIG. 10 is a front elevational view of the powered toothbrush of FIG. 7 exposing the position of the motor and batteries.
Figure 11:
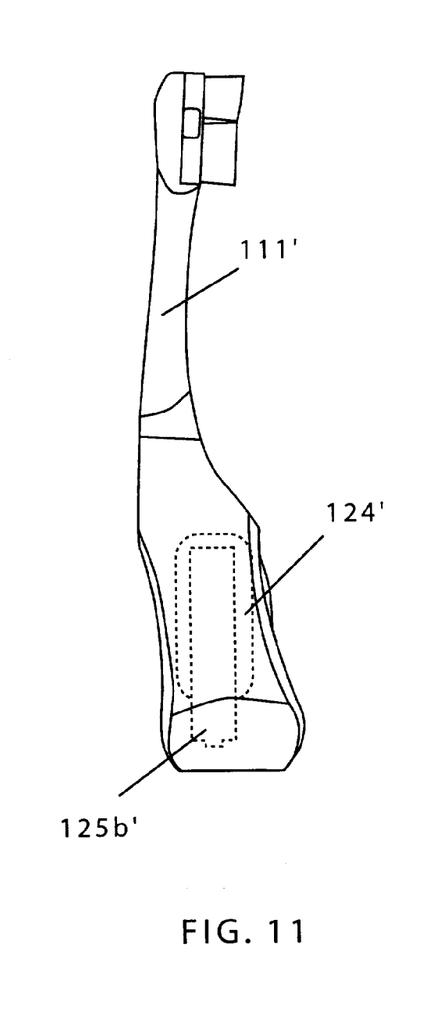
FIG. 11 is a side elevational view of the powered toothbrush of FIG. 7 exposing the position of the motor and batteries.
Figure 12:
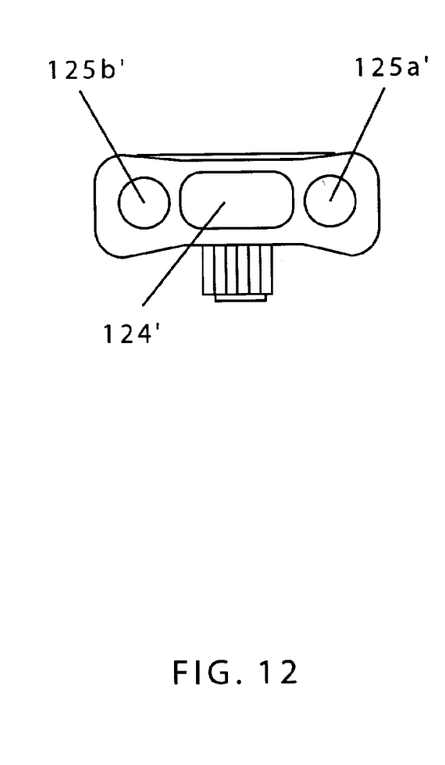
FIG. 12 is a bottom view of the powered toothbrush of FIG. 7 exposing the position of the motor and batteries.

The dimensions of the "slim" design also allow two AAA batteries 125a' and 125b' for powering the motor 124' for driving the drive shaft to be accommodated within the handle portion 102' in an upright side-by-side relationship (see FIGS. 10-12). Accordingly, the "slim" design also provides a powered toothbrush which reduces noise and vibration in comparison to existing powered toothbrushes wherein the two batteries are coaxially aligned in an elongated handle portion. Nevertheless, in both the "pod" and "slim" designs, a conventional motor and AAA batteries can be utilized.

As is shown in FIG. 8, the front face 127' in the "slim" design includes a depression 128' for comfortable thumb placement. This depression 128' also includes a single on/off switch 132' extending therefrom. As a result, user interface is simplified In addition, the rear surface 129' includes a concave depression 130'. Therefore, the depth of the handle portion 102' is restricted between the depression 128' and 130' (see H-H in FIG. 8) and is within the range of between approximately 20 to 50 mm, and most preferably 28 mm. However, it is contemplated that the on/off switch 132' can also be provided along the side faces, bottom face or rear face of the handle portion 102'.

Other powered toothbrushes in accordance with the present invention which have a lower center of gravity than existing elongated powered toothbrushes and exhibit improved ergonomics as shown in FIGS. 13 through 19 of this application. Each of the powered toothbrushes of FIGS. 13 through 19 have a substantially flat base member to provide stable support for the powered toothbrush when it is not in use and stored on a horizontal surface. In addition, each of the powered toothbrushes of FIGS. 13 through 19 have a base member which has a width which is less than the greatest width of the handle portion and a depth which is less than the greatest depth of the handle portion. Further, each of the handle portions of the powered toothbrush of FIGS. 13 through 19 have a height dimension which is less than the height dimension of the neck portion of those toothbrushes. Thus, these powered toothbrushes have a shorter and stubbier handle design which provides a lower center of gravity than existing elongated powered toothbrushes and thus assists the user in using the powered toothbrush in an improved and gentler manner.

Figure 13:
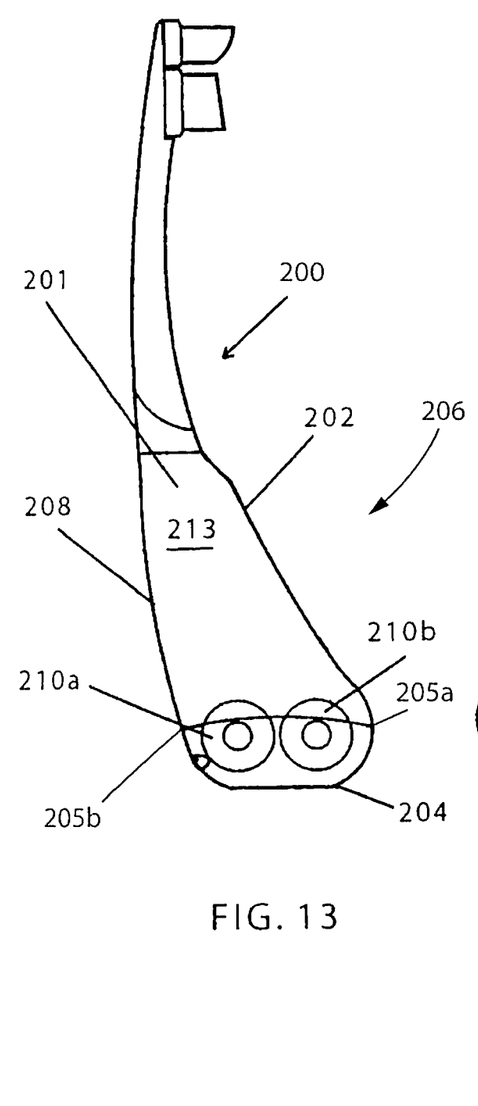
FIG. 13 is a front elevational view of a further preferred embodiment of a powered toothbrush in accordance with the teachings of the present invention.
Figure 14:
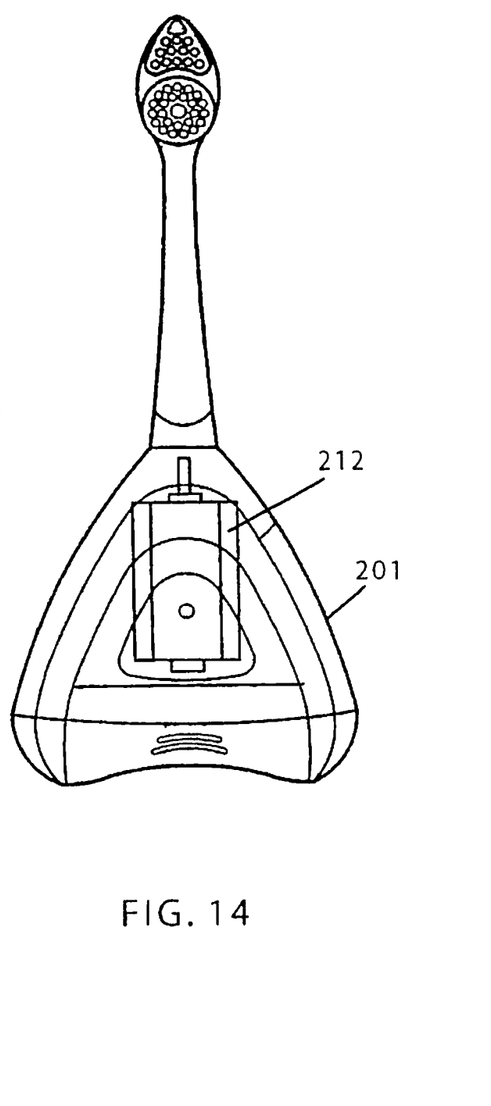
FIG. 14 is a side elevational view of the powered toothbrush of FIG. 13.

In particular, the handle portion 201 of the powered toothbrush 200 of FIGS. 13 and 14 has a front face 202 which has a greater curvature from the base member 204 to the end 205a of the handle section 206 than the curvature of the rear face 208 from the base member 204 to the end 205h of the handle portion 206. Such a design permits two AA batteries 210a and b to be accommodated within the handle portion 201 lying side-by-side adjacent the base member 204 in a generally horizontal orientation. FIG. 14 illustrates that the motor 212 can be accommodated above the batteries 210a and b in an area 213 of the handle portion with a narrowed depth.

Figure 15:
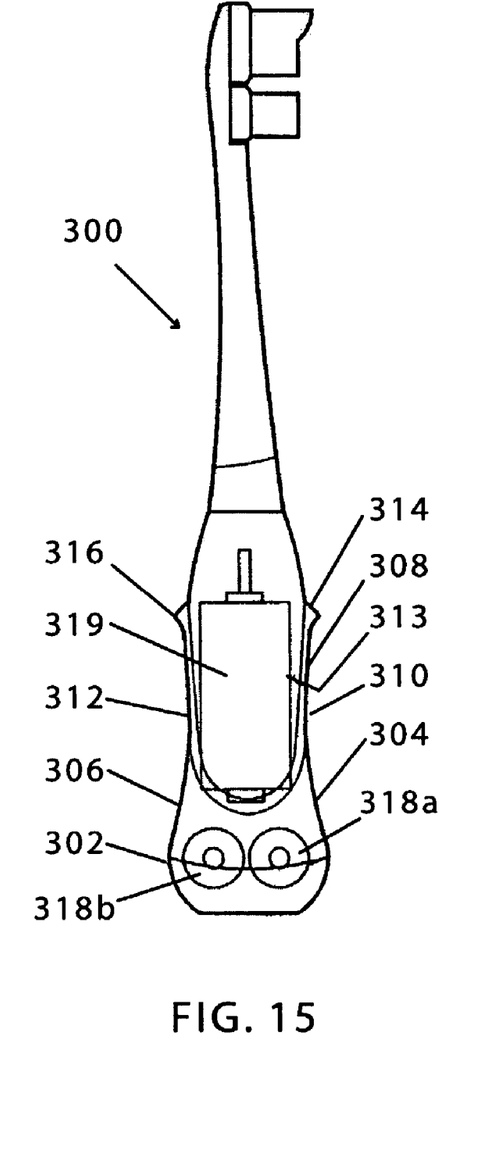
FIG. 15 is a front elevational view of another preferred embodiment of a powered toothbrush in accordance with the teachings of the present invention.
Figure 16:
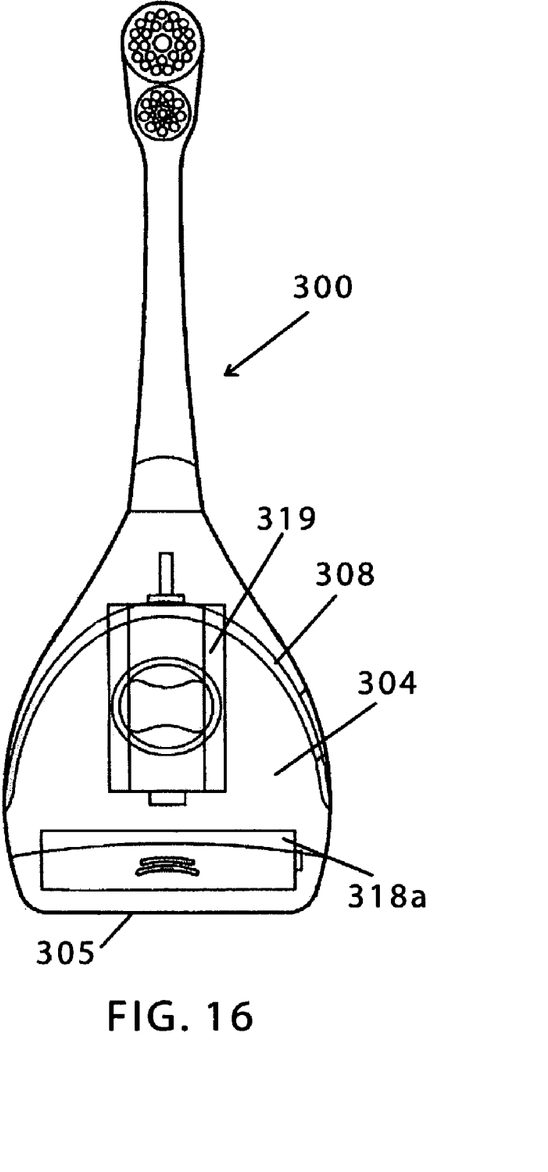
FIG. 16 is a side elevational view of the powered toothbrush of FIG. 15.

The powered toothbrush 300 of FIGS. 15 and 16 has an enlarged bulbous area 302 provided between the front and rear faces 304 and 306 of the handle portion 308 adjacent base member 305. This enlarged bulbous section 302 permits two AAA batteries 318a and b to be accommodated side-by-side adjacent to the base member 305 in a horizontal orientation. A central depression 310 and 312 is formed in the front and rear sections of the powered toothbrush 300 upwardly of the bulbous section 302. The concave depressions 310 and 312 are so formed to conform to a user's hand grip and palm configuration. The interior space 313 of the handle portion 308 between the concave depression 310 and 312 accommodates the motor 319 for driving the drive shaft which moves at least one bristle carrier. Thumb rests 314 and 316 are provided at an end of the concave depressions 310 and 312 and extend outwardly therefrom.

Figure 17:
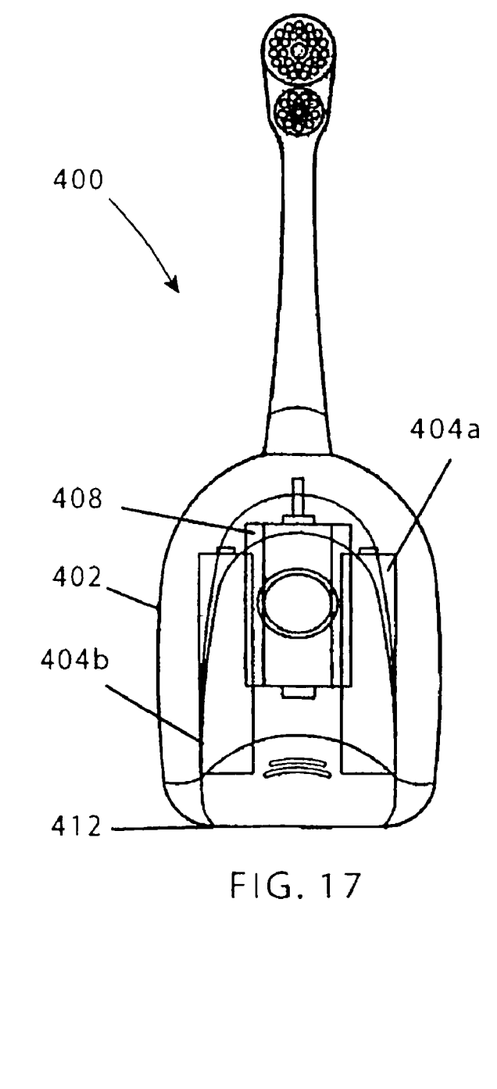
FIG. 17 is a front elevational view of yet a further preferred embodiment of a powered toothbrush in accordance with the teachings of the present invention.
Figure 18:
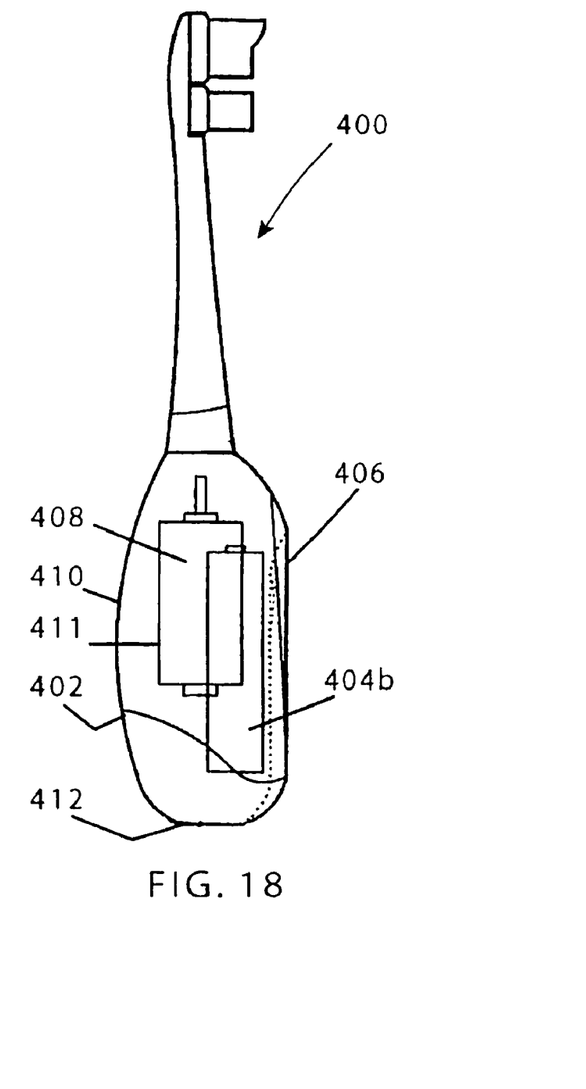
FIG. 18 is a side elevational view of the powered toothbrush of FIG. 17.
Figure 19:
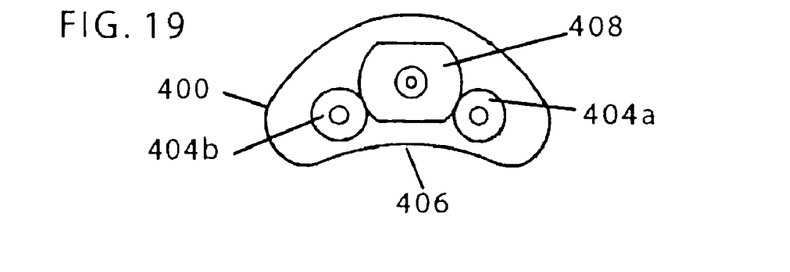
FIG. 19 is a bottom view of the powered toothbrush of FIG. 17.

Another shorter and stubbier design for the handle portion of a powered toothbrush is shown in FIGS. 17 through 19. As viewed from the bottom in FIG. 18, the handle portion 402 of this powered toothbrush 400 is of a crescent shape. This crescent shape configuration permits two AAA batteries 404a and b to be provided in an upright orientation more adjacent to the front face 406 of the handle section 402. A motor 408 is accommodated between the AAA batteries in an upright orientation and slightly therebehind (that is, the rear surface 411 of the motor 408 is more closely adjacent the rear face 410 of the handle portion 402 than the rear edges of the AAA batteries. As shown in FIGS. 17-19, the base member 412 of the handle portion 402 is substantially flat. In addition, the front face 406 is substantially flat while the rear face 410 has a generally convex surface so as to provide an improved hand gripping configuration.

Therefore, in accordance with one of the general objects of the present invention, a powered toothbrush has been provided with improved ergonomics, and a shorter and stubbier handle which will assist the user in using a powered brush in an improved and gentler manner. The powered toothbrush is reduced in size, and uses a conventional motor and batteries. User interface is also simplified and noise and vibration in the powered toothbrush are reduced.

Although the invention has been particularly shown and described with reference to certain preferred embodiments, it will be readily appreciated by those of ordinary skill in the art that various changes and modifications may be made therein without departing from the spirit and scope of the invention. For instance, although the motor in the "pod" and "slim" designs are driven by a pair of AAA batteries, the power source of these powered toothbrushes is not limited to AAA batteries. The powered toothbrush of the present invention can be adapted to use batteries of a variety of sizes and combinations which provides sufficient power requirements, for instance, one AA battery, two AA batteries, one 9V battery or one C battery. It is intended that the claims be interpreted as including the foregoing as well as any such changes and modifications.

What is claimed is:

1. A powered toothbrush comprising:
   a handle portion having a base member at one end thereof, a front face and a rear face;
   a neck portion extending from the other end of said handle portion with a head coupled to the neck portion and having a front face aligned with the front face of the handle portion and a rear face aligned with the rear face of the handle portion, the head including at least one bristle carrier connected to a drive shaft for moving the at least one bristle carrier in a first rotational direction, bristles of the bristle carrier extending outwardly from the front face of the neck portion; and
   wherein a longitudinal axis is coaxial with said handle and neck portions at all times during powered use and said handle portion is asymmetrical about said longitudinal axis with the majority of the handle portion extending in the direction of said rear face of the handle portion when viewing the powered toothbrush from the side, and said base member of said handle portion is substantially flat throughout;
   each of said base member and said handle portion have a width, measured along the front face of the handle portion, which intersects said longitudinal axis and is parallel to said bristle carrier and wherein the width of said handle portion, measured along the front face of the handle portion, varies along the length of the handle portion and wherein the width of said base member is less than the greatest width of said handle portion, and wherein the width of the base member is approximately 20 to 50 mm and the greatest width of the handle portion is approximately 25 to 60 mm;
   each of said base member and said handle portion have a depth, measured from the front face to the rear face of the handle portion, which intersects said longitudinal axis and is perpendicular to said bristle carrier and wherein the depth of said base member is less than the greatest depth of said handle portion, the depth of the handle portion from the longitudinal axis to the rear face of the handle portion is greater than the depth of the handle portion from the longitudinal axis to the front face of the handle portion, and the depth of the base member is approximately 20 to 50 mm and the greatest depth of the handle portion is approximately 25 to 60 mm; and
   said neck portion has a height dimension measured along the longitudinal axis that is greater than a height dimension of the handle portion measured along the longitudinal axis, the height dimension of the neck portion is approximately 50 to 110 mm and the height dimension of the handle portion is approximately 30 to 100 mm.

2. The powered toothbrush of claim 1 wherein said width of said base member is approximately 37 mm and the greatest width of said handle portion is approximately 43 mm.

3. The powered toothbrush of claim 1, wherein the depth of said base member is approximately 37 mm and the greatest depth of said handle portion is approximately 43 mm.

* * * * *